United States Patent [19]

Petitpierre et al.

[11] 4,252,975

[45] Feb. 24, 1981

[54] 3-INDOLYL-3-BIS-AMINO-PHENYL-PHTHALIDE COMPOUNDS

[75] Inventors: Jean C. Petitpierre, Kaiseraugst, Switzerland; Robert Garner, Bury, England

[73] Assignee: Ciba-Geigy Corporation, Ardsley, N.Y.

[21] Appl. No.: 971,768

[22] Filed: Dec. 21, 1978

Related U.S. Application Data

[62] Division of Ser. No. 758,259, Jan. 10, 1977, Pat. No. 4,153,609.

[30] Foreign Application Priority Data

Jan. 16, 1976 [CH] Switzerland ........................... 516/76

[51] Int. Cl.$^3$ ........................................... C07D 417/00

[52] U.S. Cl. ........................................... 544/62

[58] Field of Search ................. 260/326.14 R; 544/62, 544/143, 373; 546/201

[56] References Cited

U.S. PATENT DOCUMENTS

| | | | |
|---|---|---|---|
| 4,046,776 | 9/1977 | Garner et al. | 260/326.14 R |
| 4,062,866 | 12/1977 | Garner et al. | 260/326.14 R |
| 4,186,134 | 1/1980 | Garner et al. | 260/326.14 X |
| 4,189,171 | 2/1980 | Crounse et al. | 260/326.14 |

FOREIGN PATENT DOCUMENTS

| | | | |
|---|---|---|---|
| 7300523 | 5/1970 | Japan | 260/326.14 R |

*Primary Examiner*—Ethel G. Love

*Attorney, Agent, or Firm*—Prabodh I. Almaula; Edward McC. Roberts

[57] ABSTRACT

A 3-indolyl-3-bis-aminophenyl-phthalide compound of the formula

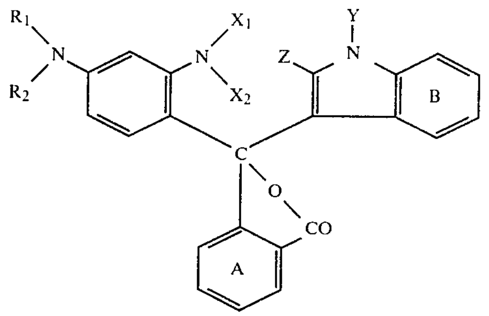

(1)

wherein $R_1$ represents alkyl which has at most 12 carbon atoms and is unsubstituted or substituted by halogen, hydroxyl, cyano or lower alkoxy, cycloalkyl, or unsubstituted or substituted phenyl or benzyl wherein the substituents are halogen, nitro, lower alkyl or lower alkoxy, $R_2$ represents hydrogen, alkyl which has at most 12 carbon atoms and is unsubstituted or substituted by halogen, hydroxyl, cyano or lower alkoxy, cycloalkyl, or benzyl which is unsubstituted or substituted by halogen, nitro, lower alkyl or lower alkoxy, or $R_1$ and $R_2$ together with the nitrogen atom linking them represent a 5- or 6-membered heterocyclic radical, $X_1$ and $X_2$ independently of one another represent hydrogen, lower alkyl, cycloalkyl, benzyl which is unsubstituted or substituted by halogen, nitro, lower alkyl or lower alkoxy, or acyl having 1 to 8 carbon atoms, and $X_1$ also represents phenyl which is unsubstituted or substituted by halogen, nitro, lower alkyl or lower alkoxy, Y represents hydrogen, alkyl which has at most 12 carbon atoms and is unsubstituted or substituted by halogen, hydroxyl or cyano, or benzyl which is unsubstituted or substituted by halogen, nitro, lower alkyl or lower alkoxy, Z represents hydrogen, lower alkyl or phenyl, and the rings A and B independently of one another are unsubstituted or substituted by halogen, nitro, amino or lower alkylamino; these compounds are particularly useful as color formers which give intense green-blue, blue or violet-blues shades of excellent fastness to light when they are brought into contact with an electron-accepting co-reactant.

7 Claims, No Drawings

3-INDOLYL-3-BIS-AMINO-PHENYL-PHTHALIDE COMPOUNDS

This is a division of application Ser. No. 758,259 filed on Jan. 10, 1977, now U.S. Pat. No. 4,153,609.

The present invention relates to novel 3-indolyl-3-bis-aminophenyl-phthalide compounds, to processes for their production and to their use in pressure-sensitive or heat-sensitive recording materials.

The novel phthalide compounds correspond to the general formula

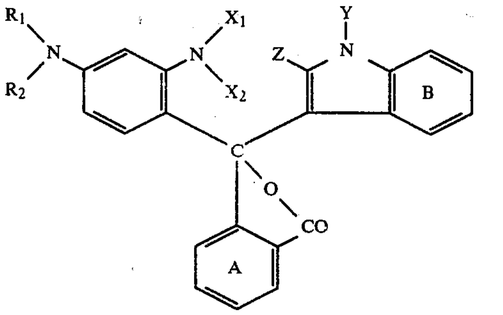

(1)

wherein

- $R_1$ represents alkyl which has at most 12 carbon atoms and is unsubstituted or substituted by halogen, hydroxyl, cyano or lower alkoxy, cycloalkyl, or phenyl or benzyl which are unsubstituted or substituted by halogen, nitro, lower alkyl or lower alkoxy,
- $R_2$ represents hydrogen, alkyl which has at most 12 carbon atoms and is unsubstituted or substituted by halogen, hydroxyl, cyano or lower alkoxy, cycloalkyl, or benzyl which is unsubstituted or substituted by halogen, nitro, lower alkyl or lower alkoxy, or
- $R_1$ and $R_2$ together with the nitrogen atom linking them represent a 5- or 6-membered, preferably saturated, heterocyclic radical,
- $X_1$ and $X_2$ independently of one another represent hydrogen, lower alkyl, cycloalkyl, benzyl which is unsubstituted or substituted by halogen, nitro, lower alkyl or lower alkoxy, or acyl having 1 to 8 carbon atoms, and $X_1$ also represents phenyl which is unsubstituted or substituted by halogen, nitro, lower alkyl or lower alkoxy,
- Y represents hydrogen, alkyl which has at most 12 carbon atoms and is unsubstituted or substituted by halogen, hydroxyl or cyano, or benzyl which is unsubstituted or substituted by halogen, nitro, lower alkyl or lower alkoxy,
- Z represents hydrogen, lower alkyl or phenyl, and the rings A and B independently of one another can be further substituted by halogen, nitro, amino or lower alkylamino.

In the definition of the radicals of the phthalide compounds, lower alkyl and lower alkoxy represent as a rule those groups or constituents of groups which contain 1 to 5, especially 1 to 3, carbon atoms, such as methyl, ethyl, n-propyl, isopropyl, n-butyl, sec.-butyl or amyl; or methoxy, ethoxy or isopropoxy.

If the substituents $R_1$, $R_2$ and Y represent alkyl groups, they can be straight-chain or branched-chain alkyl radicals. Examples of such alkyl radicals are methyl, ethyl, n-propyl, isopropyl, n-butyl, sec.-butyl, n-hexyl, n-octyl or n-dodecyl.

If the alkyl radicals in $R_1$, $R_2$ and Y are substituted, they are, in particular, cyanoalkyl, halogenoalkyl, hydroxyalkyl or alkoxyalkyl containing in each case 2 to 4 carbon atoms, such as β-cyanoethyl, β-chloroethyl, β-hydroxyethyl, β-methoxyethyl or β-ethoxyethyl.

Examples of cycloalkyl represented by the R and X radicals are cyclopentyl, or preferably cyclohexyl.

Preferred substituents in the benzyl group of the R, X and Y radicals and in the phenyl group of $R_1$ and $X_1$ are, e.g., halogens, nitro, methyl or methoxy. Examples of such araliphatic and aromatic radicals are p-methylbenzyl, o- or p-chlorobenzyl, o- or p-nitrobenzyl, o- or p-tolyl, xylyl, o-, m- or p-chlorophenyl or o- or p-nitrophenyl.

If the substituents $R_1$ and $R_2$ together with the common nitrogen atom represent a heterocyclic radical, this is for example pyrrolidino, piperidino, pipecolino, morpholino, thiomorpholino or piperazino.

The substituents $R_1$ and $R_2$ are preferably benzyl or lower alkyl. The N-substituent Y is, in particular, benzyl or alkyl having 1 to 8 carbon atoms, e.g. n-octyl, or especially methyl or ethyl.

Of the radicals $X_1$ and $X_2$, one is preferably acyl and the other is hydrogen or lower alkyl. The acyl radical is, in particular, lower alkylcarbonyl, such as formyl, acetyl or propionyl, or benzoyl.

Further acyl radicals are lower alkylsulphonyl, such as methylsulphonyl or ethylsulphonyl as well as phenylsulphonyl. Benzoyl and phenylsulphonyl can be substituted in the benzene ring by halogen, methyl or methoxy.

The rings A and B are preferably not further substituted or are further substituted by halogen e.g. chlorine. The ring A can with advantage also contain a nitro group. In this case, the phthalides preferably constitute mixtures of two isomers, with the nitro groups of the phthalic acid anhydride radical being arranged either in the positions 4 and 7 or 5 and 6.

Colour formers comprising phthalide compounds of the formula (1) which are important in practice correspond to the general formula

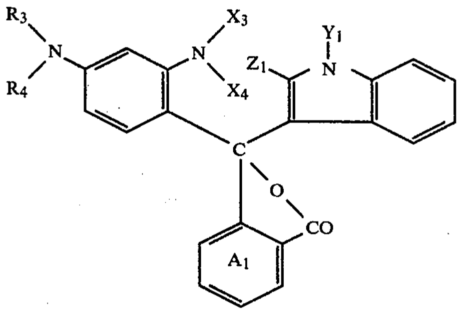

(2)

wherein

- $R_3$ and $R_4$ independently of one another represent lower alkyl, or benzyl which is unsubstituted or substituted by halogen, nitro, methyl or methoxy,
- $X_3$ and $X_4$ independently of one another represent hydrogen, lower alkyl, lower alkylcarbonyl, or benzoyl which is unsubstituted or substituted by halogen, methyl or methoxy, $Y_1$ represents hydrogen, alkyl having 1 to 8 carbon atoms, or benzyl which is unsubstituted or substituted by halogen, nitro, methyl or methoxy, $Z_1$ represents lower alkyl or phenyl, and the benzene ring $A_1$ can be substituted by nitro or by 1 to 4 halogen atoms.

Among the phthalide compounds of the formula (2), those are preferred wherein $X_3$ represents lower alkylcarbonyl, or benzoyl which is unsubstituted or substituted by halogen, methyl or methoxy, and $X_4$ represents hydrogen or lower alkyl, and $A_1$, $R_3$, $R_4$, $Y_1$ and $Z_1$ have the given meanings.

Halogens in conjunction with the foregoing substituents in the formulae (1) and (2) are, for example, fluorine, bromine or preferably chlorine.

Of particular interest are phthalide compounds of the general formula

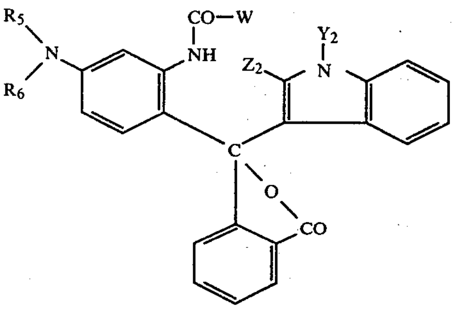
(3)

wherein $R_5$ and $R_6$ independently of one another represent lower alkyl or benzyl, W represents methyl, ethyl or phenyl, $Z_2$ represents methyl or phenyl, and $Y_2$ represents hydrogen, alkyl having 1 to 8 carbon atoms or benzyl.

Particularly preferred compounds among these compounds of the formula (3) are those wherein $R_5$ and $R_6$ represent methyl or ethyl; W represents methyl; $Z_2$ represents methyl; and $Y_2$ represents methyl, ethyl or benzyl.

The phthalide compounds of the formulae (1) to (3) according to the invention constitute novel compounds and can be produced by methods known per se. One process for the production of the phthalide compounds of the formula (1) comprises reacting a compound of the general formula

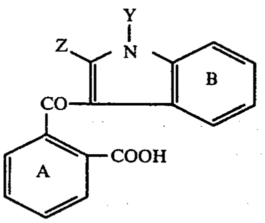
(4)

with a compound of the general formula

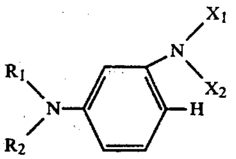
(5)

wherein A, B, Z, Y, $R_1$, $R_2$, $X_1$ and $X_2$ have the given meanings. If $X_1$ and/or $X_2$ represent hydrogen, the reaction product can subsequently be alkylated or aralkylated and/or acylated.

Alternatively, the phthalide compounds according to the invention can be produced by a process wherein a compound of the general formula

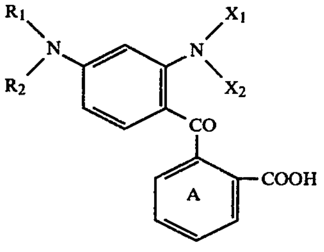
(6)

is reacted with an indole compound of the general formula

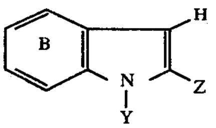
(7), wherein A, B, $R_1$, $R_2$, $X_1$, $X_2$, Y and Z have the given meanings; and the reaction product can then be alkylated or aralkylated and/or acylated if $X_1$ and/or $X_2$ represent(s) hydrogen.

The reactions are preferably so carried out that the reactants are reacted in the presence of an acid dehydrating agent. Examples of such condensation agents are acetic anhydride, sulphuric acid, zinc chloride or phosphorus oxychloride.

The alkylation or aralkylation or acylation of the reaction products wherein $X_1$ and $X_2$ represent hydrogen is performed as a rule by known processes. For example, the reaction is performed in the presence of an acid-binding agent, such as an alkali carbonate or a tertiary nitrogen base such as pyridine, and optionally in the presence of an inert organic solvent such as acetone, isopropyl alcohol, chlorobenzene or nitrobenzene. Suitable acylating agents are, e.g., reactive functional derivatives of aliphatic carboxylic acids, especially fatty acid halides and fatty acid anhydrides, such as acetyl bromide, acetyl chloride or acetic acid anhydride, or of aromatic carboxylic acids such as benzoic acid halides. Suitable alkylating agents are alkyl halides such as methyl or ethyl iodide or methyl or ethyl chloride, or dialkyl sulphates such as dimethyl sulphate or diethyl sulphate. Aralkylating agents which are suitable are, in particular, benzyl chloride and the corresponding substitution products such as p-chlorobenzyl chloride or 2,4-dimethylbenzyl chloride, which are preferably used in a nonpolar organic solvent such as benzene, toluene or xylene.

The starting materials of the formulae (4) and (6) are obtained as a rule by reaction of an anhydride of the general formula

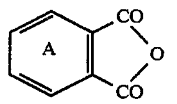

(8)

with a compound of the formula (7) or with a compound of of the formula (5), with the reaction being advantageously performed in an organic solvent, optionally in the presence of a Lewis acid, e.g. aluminium chloride. Suitable organic solvents are, e.g., benzene, toluene, xylene or chlorobenzene. The reaction is performed preferably at or below the boiling point of the employed solvent. The compounds of the formula (4) wherein Y represents an optionally substituted alkyl or benzyl group are preferably produced by alkylation or aralkylation of the intermediate by customary methods, which intermediate is obtained by reaction of an anhydride of the formula (8) with an indole of the formula (7) wherein Y represents hydrogen. The alkylating and aralkylating agents can be the same as those given for the production of the phthalide compounds of the formulae (1) to (3).

The phthalide compounds of the formulae (1) to (3) are usually colourless or at most slightly coloured. If these colour formers are brought into contact with an acid developer, i.e. with an electron acceptor, they yield green-blue, blue or violet-blue shades which have excellent fastness to light. They are therefore also very valuable in admixture with other known colour formers, e.g. with crystal violet lactone, 3,3-(bis-aminophenyl-)phthalide. 2,6-diaminofluorans or benzoylleucomethylene blue, in order to produce blue, navy blue, grey or black dyeings.

These colour formers are suitable, in particular, for application in a pressure- or heat-sensitive recording material, which can be both copying and registering material.

A pressure-sensitive material comprises, for example, at least one pair of sheets which contain at least one colour former of the formulae (1) to (3) dissolved in an organic solvent and an electron-acceptor substance as the developer. The colour former gives a coloured marking at the points at which it comes into contact with the electron-acceptor substance.

Typical examples of such developers are attapulgite clay, silton clay, silicon dioxide, bentonite, halloysite, aluminium oxide, aluminium sulphate, aluminium phosphate, zinc chloride, kaolin or any desired acid clay or a polymeric material having an acid reaction, such as a phenolic polymer, an alkylphenolacetylene resin, a maleic acid/rosin resin or a partially or completely hydrolysed polymer of maleic anhydride with styrene, ethylene, vinyl methyl ether or carboxypolymethylene. Preferred developers are attapulgite clay, silton clay or a phenolformaldehyde resin.

These electron acceptors are preferably applied in the form of a layer to the face of the receiving sheet.

In order to avoid the colour formers contained in the pressure-sensitive recording material becoming prematurely active, they are as a rule separated from the electron-acceptor substance. This separation can be advantageously effected by incorporating the colour formers into foam-, sponge- or honeycombe-like structures. Preferably, however, the colour-formers are enclosed in micro-capsules which as a rule break under pressure.

When the capsules are broken as a result of pressure, for example by means of a pencil, and when the colour-former solution is transferred in this way to an adjacent sheet which is coated with an electron acceptor, a coloured spot or area is produced. This colour results from the dye being formed, which dye absorbs in the visible range of the electromagnetic spectrum.

The colour formers are preferably encapsulated in the form of solutions in organic solvents. Examples of suitable solvents are preferably nonvolatile solvents, e.g. polyhalogenated diphenyl such as trichlorodiphenyl or a mixture thereof with liquid paraffin, also tricresyl phosphate, di-n-butyl phthalate, dioctyl phthalate, trichlorobenzene, nitrobenzene, trichloroethyl phosphate, petroleum ether, hydrocarbon oils such as paraffin, alkylated derivatives of diphenyl, naphthalene or triphenyl, terphenyls, partially hydrogenated terphenyl or other chlorinated or hydrogenated, fused aromatic hydrocarbons.

The capsule walls can be evenly formed around the droplets of the colour-former solution by means of coacervation forces, and the encapsulating material can consist of, for example, gelatin and gum arabic, as described, e.g., in the U.S. Pat. No. 2,800,457. The capsules can preferably also be formed from an aminoplast or modified aminoplasts by polycondensation, as described in the British Pat. Specifications Nos. 989,264 and 1,156,725.

The micro-capsules containing the colour formers of the formula (1) can be used to produce pressure-sensitive copying materials of the most varied known types. The various systems differ from one another essentially in the arrangement of the capsules and of the colour reactants and in the carrier material.

A preferred arrangement is that in which the encapsulated colour former is applied in the form of a layer to the back of a transfer sheet and the electron-acceptor substance is applied in the form of a layer to the front of a receiving sheet. The constituents can however also be used in the paper pulp.

Another arrangement of the constituents is that wherein the micro-capsules containing the colour former is present together with the developer in or on the same sheet in the form of one or more individual layers, or in the paper pulp.

Such pressure-sensitive copying materials are described, for example, in the U.S. Pat. Nos. 2,730,457, 2,932,582, 3,418,250, 3,418,656, 3,427,180 and 3,516,846. Further systems are described in the British Pat. Specifications Nos. 1,042,596, 1,042,597, 1,042,598, 1,042,599, 1,053,935 and 1,517,650. Micro-capsules containing the colour formers of the formula (1) are suitable for each of these systems and for other pressure-sensitive systems.

The capsules are preferably attached to the carrier by means of a suitable adhesive. Since paper is the preferred carrier material, these adhesives are principally paper-coating agents, such as gum arabic, polyvinyl alcohol, hydroxymethylcellulose, casein, methylcellulose or dextrin.

The term "paper" used here comprises not only normal papers made from cellulose fibres but also papers in which the cellulose fibres are replaced (partially or completely) by fibres of synthetic polymers.

The phthalide compounds of the formulae (1) to (3) can be used as colour formers also in a thermo-reactive recording material. This contains as a rule at least one carrier, a colour former, an electron-acceptor substance and, optionally, also a binder. Thermo-reactive recording systems include, e.g., heat-sensitive recording and copying materials and papers. These systems are employed, for example, for the recording of information, e.g. in computers, teleprinters or telex machines, or in measuring instruments. The reproduction of the image (reproduction of the marking) can also be effected manually using a heated pen. A further means of reproducing markings by means of heat is the application of Laser beams.

The thermo-reactive recording material can be formed in such a way that the colour former is dissolved or dispersed in a layer of binder, and the developer is dissolved or dispersed in the binder in a second layer. A further possibility is for both the colour former and the developer to be dispersed in one layer. The binder is softened in specific areas by means of heat and at these points, to which heat is applied, the colour former comes into contact with the electron-acceptor substance and the desired colour develops immediately.

The developers are the same electron-acceptor substances as are used in pressure-sensitive papers. Examples of developers are the clay minerals and phenol resins already mentioned, or phenolic compounds, such as 4-tert.-butylphenol, 4-phenylphenol, 4-hydroxydiphenyl ether, α-naphthol, β-naphthol, 4-hydroxybenzoic acid methyl ester, 4-hydroxyacetophenone, 2,2'-dihydroxydiphenyl, 4,4'-isopropylidenediphenol, 4,4'-isopropylidene-bis-(2-methylphenol), 4,4'-bis-(hydroxyphenyl)-valeric acid, hydroquinone, pyrogallol, phloroglucinol, p-, m- and o-hydroxybenzoic acid, gallic acid, 1-hydroxy-2-naphthoic acid and also boric acid and aliphatic dicarboxylic acids, such as tartaric acid, oxalic acid, maleic acid, citric acid, citraconic acid or succinic acid.

Preferably used for the production of the thermoreactive recording material are film-forming binders which can be melted. These binders are usually water-soluble, whereas the phthalide compounds and the developer are insoluble in water. The binder should be capable of dispersing and fixing the colour former and the developer at room temperature.

The binder softens or melts under the action of heat, so that the colour former comes into contact with the developer and can form a colour. Binders which are soluble in water or at least swellable in water are, e.g., hydrophilic polymers, such as polyvinyl alcohol, polyacrylic acid, hydroxyethylcellulose, methylcellulose, carboxymethylcellulose, polyacrylamide, polyvinylpyrrolidone, gelatin and starch.

If the colour former and the developer are in two separate layers, it is possible to use binders which are insoluble in water, that is to say binders which are soluble in non-polar or only slightly polar solvents, such as natural rubber, synthetic rubber, chlorinated rubber, alkyd resins, polystyrene, styrene/butadiene copolymers, polymethyl methacrylates, ethylcellulose, nitrocellulose and polyvinylcarbazole. The preferred arrangement is however that whereby the colour former and the developer are contained in one layer in a water-soluble binder.

The thermo-reactive layers can contain further additives. In order to improve the degree of whiteness, to facilitate printing of the papers and to prevent sticking of the heated pen, these layers can contain, e.g., talc, $TiO_2$, ZnO or $CaCC_3$, or organic pigments such as urea-formaldehyde polymers. In order to ensure that the colour is formed only within a limited temperature range, it is possible to add substances such as urea, thiourea, acetanilide, phthalic anhydride or other corresponding fusible products which induce the simultaneous melting of the colour former and the developer.

Except where otherwise stated, the percentages given in the following Examples relate to weight.

EXAMPLE 1

A mixture of 6.15 g of 3-(2'-carboxybenzoyl)-1-ethyl-2-methyl-indole, 4.12 g of 3-diethylaminoacetanilide and 9.6 ml of acetic anhydride is stirred for 2 hours at 60° C. After cooling to room temperature, an addition is made of 20 ml of methanol, whereupon the solution is poured into 86 ml of water. The resulting precipitate is then filtered off, washed with water and dried to give 8.05 g of a compound of the formula

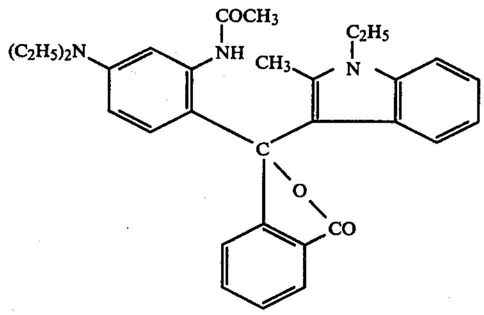
(11)

A specimen recrystallised from cyclohexane melts at 165°-168° C. This colour former develops on silton clay a blue colour of λ max. 600 nm.

EXAMPLE 2

If the 3-diethylaminoacetanilide in Example 1 is replaced by 5.36 g of 3-diethylamino-benzanilide, with the procedure otherwise being as described in Example 1, there is obtained 4.4 g of a compound of the formula

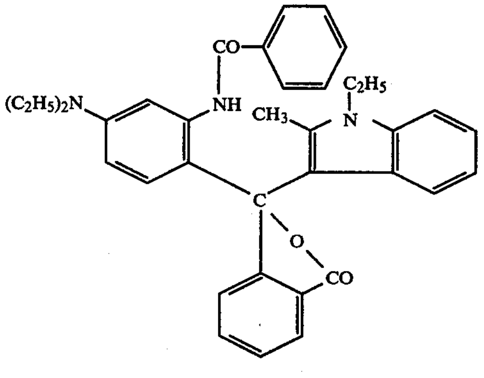
(12)

A specimen recrystallised from methanol melts at 201°-202° C. This colour former develops on silton clay a blue colour of λ max. 600 nm.

EXAMPLE 3

If the 3-(2'-carboxybenzoyl)-1-ethyl-2-methyl-indole in Example 1 is replaced by an equimolar amount of 3-(2'-carboxybenzoyl)-1-benzyl-2-methyl-indole, with the procedure otherwise being as described in Example 1, there is obtained 4.5 g of a phthalide compound of the formula (13)

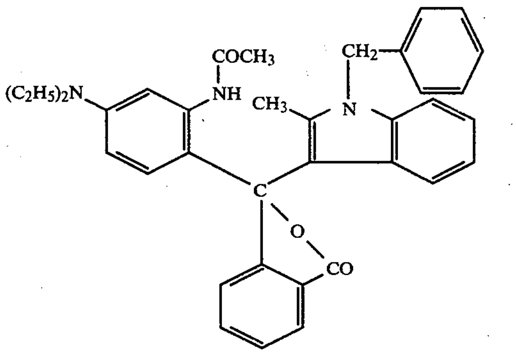

which melts at 138°–142° C. This colour former develops on silton clay a blue colour of λ max. 600 nm.

EXAMPLE 4

If the 3-(2′-carboxybenzoyl)-1-ethyl-2-methyl-indole in Example 1 is replaced by an equimolar amount of 3-(2′-carboxybenzoyl)-2-methyl-indole, with the procedure otherwise being as described in Example 1, there is obtained, after recrystallisation from ethanol, 3.3 g of a phthalide compound of the formula (14)

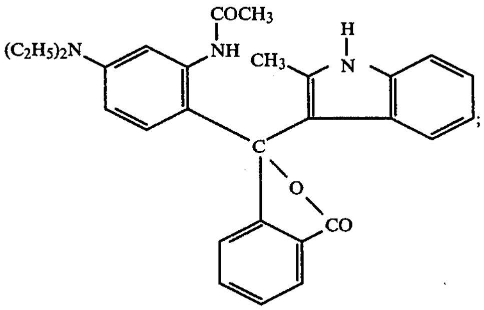

;

melting point 260°–262° C.

This colour former develops on silton clay a blue colour of λ max. 592 nm.

EXAMPLE 5

If the 3-(2′-carboxybenzoyl)-1-ethyl-2-methyl-indole in Example 1 is replaced by an equimolar amount of 3-(2′-carboxybenzoyl)-1-n-octyl-2-methyl-indole, with the procedure otherwise being as described in Example 1, there is obtained 3.8 g of a phthalide compound of the formula (15)

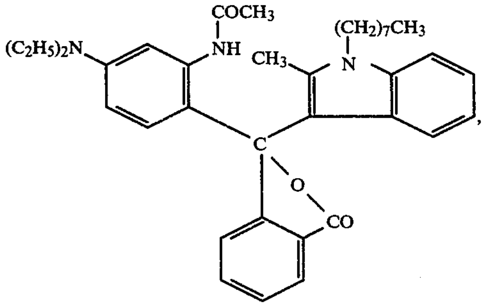

, which melts at 123°–125° C. This colour former develops on silton clay a blue colour of λ max. 600 nm.

EXAMPLE 6

If the 3-(2′-carboxybenzoyl)-1-ethyl-2-methyl-indole in Example 1 is replaced by an equimolar amount of 3-(2′-carboxybenzoyl)-1-n-pentyl-2-methyl-indole, with the procedure otherwise being as described in Example 1, there is obtained 3.6 g of a phthalide compound of the formula (16)

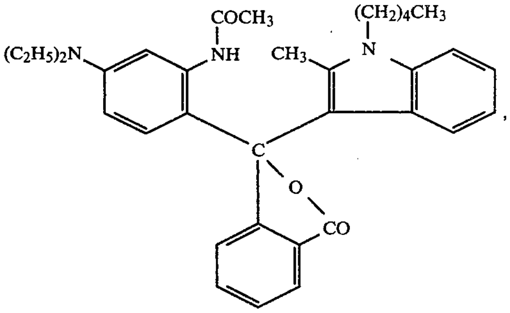

, which melts at 162°–163° C. The colour former develops on silton clay a blue colour of λ max. 600 nm.

EXAMPLE 7

Production of a pressure-sensitive copying paper

A solution of 3 g of the phthalide compound of the formula (11) in 97 g of partially hydrogenated terphenyl is emulsified in a solution of 12 g of pigskin gelatin in 88 g of water at 50° C. A solution of 12 g of gum arabic in 88 g of water at 50° C. is then added and an addition is subsequently made of 200 ml of water at 50° C. The resulting emulsion is poured into 600 g of ice water and cooled, with coacervation being thus effected. A sheet of paper is coated with the resulting suspension of micro-capsules and dried. A second sheet of paper is coated with silton clay. The first sheet of paper and the paper coated with silton clay are placed together with the coatings adjacent to one another.

By means of writing by hand or with a typewriter on the first sheet, pressure is applied and on the sheet coated with clay there develops a blue copy which has excellent fastness to light.

Corresponding blue shade effects can be obtained using any of the other colour formers of the formulae (12) to (16) given in the Examples.

EXAMPLE 8

Production of a thermo-reactive paper 6 g of an aqueous dispersion containing 1.57% of the phthalide compound of the formula (13) and 6.7% of polyvinyl alcohol is mixed with 134 g of an aqueous dispersion containing 14% of 4,4-isopropylidenediphenol, 8% of attapulgite clay and 6% of polyvinyl alcohol. This mixture is applied to a paper and dried. A blue colour having excellent fastness to light is obtained on contact of the paper with a heated ball-point pen.

Similar results are obtained using any one of the other colour formers of the formulae (11), (12) and (14) to (16) given in the Examples.

We claim:

1. A 3-indolyl-3-bis-aminophenylphthalide compound of the formula

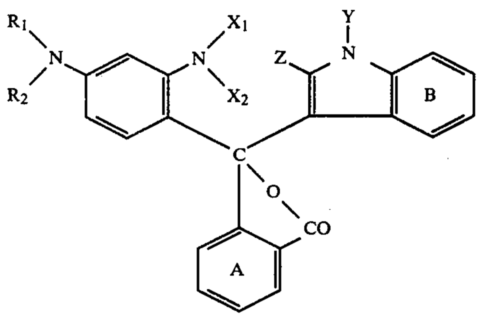

(I)

wherein $R_1$ and $R_2$ together with the nitrogen atoms linking them represent a 5- or 6-membered heterocyclic radical selected from the group consisting of pyrrolidino, piperidino, pipecolino, morpholino, thiomorpholino, or piperazino, $X_1$ and $X_2$ independently of one another represent hydrogen, lower alkyl, cycloalkyl, benzyl which is unsubstituted or substituted by halogen, nitro, lower alkyl or lower alkoxy, or acyl having 1 to 8 carbon atoms, and $X_1$ also represents phenyl which is unsubstituted or substituted by halogen, nitro, lower alkyl or lower alkoxy, Y represents hydrogen, alkyl which has at most 12 carbon atoms and is unsubstituted or substituted by halogen, hydroxyl or cyano, or benzyl which is unsubstituted or substituted by halogen, nitro lower alkyl or lower alkoxy, Z represents hydrogen, lower alkyl or phenyl, and the rings A and B independently of one another are unsubstituted or substituted by halogen, nitro, amino or lower alkylamino.

2. A phthalide compound according to claim 1, of the formula

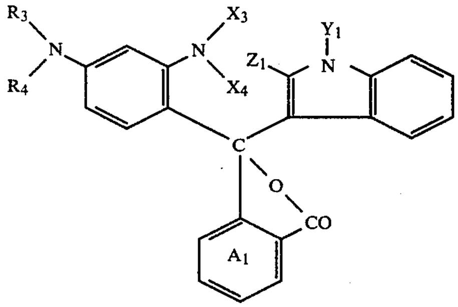

(2)

wherein $R_3$ and $R_4$ have the meaning given to $R_1$ and $R_2$ in claim 1, $X_3$ and $X_4$ independently of one another represent hydrogen, lower alkyl, lower alkylcarbonyl, or benzoyl which is unsubstituted or substituted by halogen, methyl or methoxy, $Y_1$ represents hydrogen, alkyl having 1 to 8 carbon atoms, or benzyl which is unsubstituted or substituted by halogen, nitro, methyl or methoxy, $Z_1$ represent lower alkyl or phenyl, and the benzene ring $A_1$ is unsubstituted or substituted by nitro or by 1 to 4 halogen atoms.

3. A phthalide compound according to claim 2, of the formula (2) wherein $X_3$ represents lower alkylcarbonyl, or benzoyl which is unsubstituted or substituted by halogen, methyl or methoxy, and $X_4$ represents hydrogen or lower alkyl, and $A_1$, $R_3$, $R_4$, $Y_1$ and $Z_1$ have the meanings given in claim 2.

4. A phthalidecompound according to claim 3, of the formula

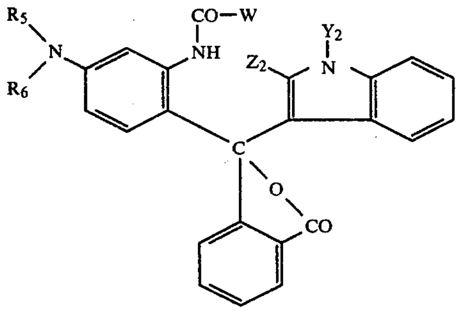

(3)

wherein $R_5$ and $R_6$ have the meaning given to $R_3$ and $R_4$ in claim 3, W represents methyl, ethyl or phenyl, $Z_2$ represents methyl or phenyl, and $Y_2$ represents hydrogen, alkyl having 1 to 8 carbon atoms or benzyl.

5. A phthalide compound according to claim 4, of the formula (3) wherein W represents methyl, $Z_2$ represents methyl and $Y_2$ represents methyl, ethyl or benzyl.

6. A phthalide compound according to claim 4, of the formula (3) wherein W represents methyl, $Z_2$ represents methyl and $Y_2$ represents ethyl.

7. A phthalide compound according to claim 4, of the formula (3) wherein W represents methyl, $Z_2$ represents methyl and $Y_2$ represents n-octyl.

* * * * *